United States Patent [19]

Chiu et al.

[11] Patent Number: 5,554,745
[45] Date of Patent: Sep. 10, 1996

[54] ALDEHYDE CATIONIC DERIVATIVES OF GALACTOSE CONTAINING POLYSACCHARIDES USED AS PAPER STRENGTH ADDITIVES

[75] Inventors: Chung-Wai Chiu, Westfield; Roger Jeffcoat, Bridgewater; Matthew Henley, Somerset; Leroy Peek, Milford, all of N.J.

[73] Assignee: National Starch and Chemical Investment Holding Corporation, Wilmington, Del.

[21] Appl. No.: 426,808

[22] Filed: Apr. 21, 1995

Related U.S. Application Data

[63] Continuation of Ser. No. 883,319, May 14, 1992.
[51] Int. Cl.$^6$ ............................................. D21H 21/00
[52] U.S. Cl. ........................... 536/52; 536/114; 536/124; 162/158
[58] Field of Search ...................... 536/52, 114, 124; 162/58

[56] References Cited

U.S. PATENT DOCUMENTS

| | | | |
|---|---|---|---|
| 2,803,558 | 8/1957 | Fronmuller | 106/205 |
| 2,813,093 | 11/1957 | Caldwell et al. | |
| 2,989,520 | 7/1961 | Rutenberg et al. | |
| 3,062,652 | 11/1962 | Jeffreys et al. | 96/99 |
| 3,077,469 | 2/1963 | Aszalos | |
| 3,086,969 | 4/1963 | Slager | |
| 3,236,832 | 2/1966 | Opie et al. | |
| 3,297,604 | 1/1967 | Germino | |
| 3,467,647 | 9/1969 | Benninga | 536/114 |
| 3,519,618 | 7/1970 | Parmerter | |
| 3,553,193 | 1/1971 | LeRoy et al. | |
| 3,632,802 | 1/1972 | BeMiller et al. | |
| 3,691,153 | 9/1972 | Vemuri | 536/114 |
| 3,740,391 | 6/1973 | Williams et al. | 260/233.3 R |
| 4,031,307 | 6/1977 | DeMartino et al. | 536/114 |
| 4,119,487 | 10/1978 | Tessler | 162/175 |
| 4,276,414 | 6/1981 | Tessler | 536/114 |
| 4,663,448 | 5/1987 | Chiu | 536/111 |
| 4,675,394 | 6/1987 | Solarek et al. | 536/43 |
| 4,749,800 | 7/1988 | Jobe et al. | 549/452 |
| 5,227,481 | 7/1993 | Tsai et al. | 536/18.7 |

FOREIGN PATENT DOCUMENTS 0406837  1/1991  European Pat. Off.

OTHER PUBLICATIONS

"Cationic Starches," D. B. Solarek, *Modified Starches: Properties and Uses*, Chapter 8, 1986, pp. 113–129.

Primary Examiner—Jeffrey Mullis
Attorney, Agent, or Firm—Eugene Zagarella, Jr.

[57] ABSTRACT

Aldehyde cationic derivatives of galactose containing polysaccharides which are obtained by oxidizing galactose containing polysaccharides with the enzyme galactose oxidase. The enzyme oxidized products have an aldehyde function at a specific position of the polysaccharide, i.e., the $C_6$ position, of the galactose unit, and the cationic derivatives thereof have unexpected and significantly improved properties when used as paper strength additives.

8 Claims, No Drawings

ALDEHYDE CATIONIC DERIVATIVES OF GALACTOSE CONTAINING POLYSACCHARIDES USED AS PAPER STRENGTH ADDITIVES

This application is a division, of application Ser. No. 07/883,319, filed May 14, 1992.

BACKGROUND OF THE INVENTION

This invention relates to novel aldehydic, cationic derivatives of natural occurring galactose containing polysaccharides obtained by site-specific oxidizing the selected polysaccharide with the enzyme galactose oxidase. This cation derivatized, enzyme oxidized product has an aldehyde function at a specific position of the polysaccharide and provides surprising strength properties when used as a paper additive.

The term "paper" as used herein includes sheet-like masses and molded products made from cellulosic materials which may be derived from natural sources as well as from synthetics such as polyamides, polyesters and polyacrylic resins and from mineral fibers such as asbestos and glass. In addition, papers made from combinations of cellulosic and synthetic materials are applicable herein. Paperboard is also included within the broad term "paper"

The modification of starch and other polysaccharides by many different methods to produce various cation and aldehyde containing polysaccharides as well as cationic-aldehyde containing derivatives is well known. Many of these modified polysaccharides have been used as paper additives to improve properties such as strength, drainage and pigment retention. However, it has been found that the modified polysaccharides are often not useful because they prematurely ies.

The cationic polysaccharides can be produced by reaction with reagents which will introduce a cationic group containing nitrogen, sulfur or phosphorus therein as disclosed in "Cationic Starches" by D. B, Solarek, in *Modified Starches: Properties and Use*, Chapter 8, 1986. Particularly useful cationic derivatives are the tertiary aminoalkyl starch ethers and the quaternary ammonium starch ethers.

Oxidative and non-oxidative methods have been used to introduce aldehyde groups into polysaccharides such as starches, gums and celluloses. The oxidative methods used have included treatment with periodic acid, periodates, or alkali metal ferrates. See U.S. Pat. No. 3,086,969 issued Apr. 23, 1963 to J. E. Slager which discloses an improved process for the preparation of a dialdehyde polysaccharide using periodic acid; U.S. Pat. No. 3,236,832 issued Feb. 22, 1966 to J. W. Opie et al. which discloses a method of preparing periodate modified polygalactomannan gums using periodic acid or the alkali metal salts thereof; U.S. Pat. No. 3,062,652 issued Nov. 6, 1962 to R. A. Jeffreys et al. which discloses the preparation of dialdehyde gums using periodate or periodic acid; and U.S. Pat. No. 3,632,082 issued Jan. 4, 1972 to J. N. BeMiller et. al. which discloses a method for oxidizing a carbohydrate (e.g., starch or cellulose) with an alkali metal ferrate.

The disadvantages of the oxidative method include degradation to lower molecular weight products and the formation of carboxyl groups due to further oxidation of the aldehyde groups. U.S. Pat. No. 3,553,193 issued Jan. 5, 1973 to D. H. LeRoy et al. describes a method for oxidizing starch using an alkali metal bromite or hypobromite under carefully controlled conditions. The resulting aldehyde is reported to have a substantially greater proportion of carbonyl groups, i.e., aldehyde groups, than carboxyl groups. It also discloses a method for selectively oxidizing the side chains of starch derivatives, e.g., an alkoxylated starch such as dihydroxypropyl starches, under the same process conditions whereby the underivatized starch hydroxy groups on the rings are substantially non-oxidized.

The presence of carboxylic groups in aldehyde starches has several disadvantages in addition to the obvious reduction in the degree of aldehyde substitution. This includes the introduction of hydrophilic properties due to the carboxyl groups, an upset in the cationic/anionic ratio when a cationic starch base is used (as in most papermaking wet end uses) and the possible formation of salts (in papermaking wet end use) which could give rise to ionic crosslinking.

The non-oxidative methods typically involve the chemical modification of the polysaccharide with an aldehyde-containing reagent. Generally, chemical modification is random or not site-specific. See U.S. Pat. No. 3,519,618 issued Jul. 7, 1970 to S. M. Parmerter and U.S. Pat. No. 3,740,391 issued Jun. 19, 1973 to L. L. Williams et al. which cover starch derivatives and U.S. Pat. No. 2,803,558 issued Aug. 20, 1957 to G. D. Fronmuller which covers a gum derivative. The starch derivative of Parmerter is prepared by reaction with an unsaturated aldehyde (e.g., acrolein) and has the structure:

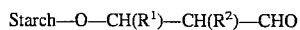

where $R^1$ and $R^2$ are hydrogen, lower alkyls or halogen. The starch derivative of Williams is prepared by reaction with acrylamide followed by reaction with glyoxal and has the structure:

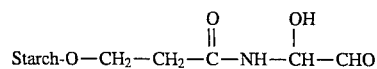

The gum derivative of Fronmuller is prepared by treating the dry gum (e.g., locust bean or guar gum) with peracetic acid to reduce the viscosity, neutralizing and then reacting with glyoxal. Water soluble cellulose ethers (e.g., hydroxyethyl cellulose) have also been reacted with glyoxal or urea formaldehyde to give aldehyde-containing derivatives.

One of the disadvantages of introducing the aldehyde groups directly using an aldehyde-containing reagent is the possibility of the derivative crosslinking prior to use. This is a particular disadvantage when the products are being used to impart temporary wet strength to paper via a crosslinking reaction with the cellulose fibers. The Williams '391 patent, cited above, alludes to this problem when it notes that solutions of the glyoxalated polymers are stable for at least a week when diluted to 10% solids by weight and adjusted to pH of 3 (Col. 3, lines 60–63). The Parmerter patent notes that the starch aldehyde is a substantially non-crosslinked granular starch derivative and discusses the importance of the non-crosslinked character (col. 2, lines 40–45)

U.S. Pat. No. 4,675,394 issued Jun. 23, 1987 to D. B. Solarek et. al. discloses a non-oxidative method for introducing block aldehyde groups into starch. This method avoids the premature reaction of the aldehyde by introducing acetal groups which are easily hydrolyzed at low pH to form the aldehyde. However, the generation of the aldehydic function at low pH also degrades the polysaccharide backbone. For certain applications, this degradation is undesirable. Cationic aldehyde containing derivatives are further disclosed as being useful as paper strength additives.

U.S. Pat. No. 3,297,604 issued Jan. 10, 1967 to F. J. Germino discloses galactose containing polysaccharides which are oxidized chemically or enzymatically with galactose oxidase. This patent further discloses the use of these oxidized products as various intermediates for crosslinking polymers, both natural and synthetic, and for improving strength properties of cellulose and paper.

U.S. Pat. No. 4,031,307 issued Jun. 21, 1977 to R. N. De Martino et. al. discloses cationic polygalactomannan compositions and more particularly a process or producing quaternary ammonium ethers of polygalactomannan gums.

The composition of a cationic modified and site-specific oxidized natural polysaccharide has not been disclosed previously and furthermore it has now been found that surprising and unexpectedly improved paper strength properties are achieved when using such polysaccharides as strength additives.

SUMMARY OF THE INVENTION

The present invention provides aldehydic cationic derivatives of galactose containing polysaccharides which are obtained by oxidizing the selected polysaccharides with the enzyme galactose oxidase. The enzyme oxidized product has an aldehyde function at a specific position of the polysaccharide, i.e., the $C_6$-OH group of the galactose unit, and the cationic derivative thereof exhibits significantly improved and surprising properties when used as a paper strength additive.

DETAILED DESCRIPTION OF THE INVENTION

The polysaccharides useful in preparing the aldehydic cationic derivatives of this invention are any of the galactose containing polysaccharides and particularly the naturally occurring galactose containing polysaccharides. These are the polysaccharides containing the galactose configuration at the $C_6$ position and which can be oxidized at the $C_6$-OH position to form an aldehyde group. Applicable galactose containing polysaccharides include polygalactomannan gums such as locust bean gum and gear gum, as well as tamarind gum and gum arabic. The polygalactomannan gums as noted above and used herein are heteropolysaccharides composed principally of long chains of mannose units and single unit side chains of galactose units and are further disclosed in U.S. Pat. 4,276,414 issued on Jun. 30, 1981 to M. Tessler.

Gear gum is one of the polysaccharides which contain the galactose configuration at the $C_4$ position and as illustrated below this galactose configuration or unit is oxidized with the enzyme galactose oxidase to form an aldehyde group at a specific position of the unit, i.e., the $C_6$-OH group:

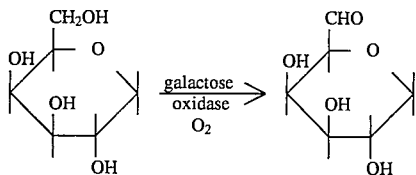

The aldehyde derivatives of galactose containing polysaccharides of this invention also contain one or more cation groups. Cationization of the selected polysaccharides can be produced by well known chemical reactions with reagents containing amino, imino, ammonium, sulfonium or phosphonium groups as disclosed, for example Solarek, "cationic starches" Supra and in U.S. Pat. No. 4,119,787 issued Oct. 10, 1097 to M. Tessler. Such cationic derivatives include those containing nitrogen containing groups comprising primary, secondary, tertiary and quaternary amines and sulfonium and phosphonium groups attached through either ether or ester linkages. The preferred derivatives are those containing the tertiary amino and quaternary ammonium ether groups.

The general method for preparing polysaccharides such as starches containing tertiary amine groups, which method typically involves reacting starch under alkaline conditions with a dialkylaminoalkyl halide is described in U.S. Pat. No. 2,813,093 issued on Nov. 12, 1957 to c. Caldwell et. al. Another method therefore is disclosed in U.S. Pat. No 4,675,394 issued Jan. 23, 1987 to D. Solarek et. al. The primary and secondary amine polysaccharides, starch, may be prepared by reacting the polysaccharide with aminoalkyl anhydrides, aminoalkyl epoxides or halides, or the corresponding compounds containing aryl in addition to the alkyl groups.

Quaternary ammonium groups may be introduced into the polysaccharide and starch molecule by suitable treatment of the tertiary aminoalkyl ether of starch, as described in the previously noted U.S. Pat. No. 2,813,093 Alternatively, quaternary groups may be introduced directly into the polysaccharide molecule by treatment with the reaction product of an epihalohydrin and a tertiary amine or tertiary amine salt, to provide for example, 3-(trimethylammonium chloride)-2-hydroxylpropyl ether substituent groups as disclosed in the noted U.S. Pat. No. 4,119,487. The above noted patents, i.e., '487, '093 and '394 are incorporated herein by reference as well as commonly assigned co-pending U.S. Pat. application Ser. No. 07/376,779 filed Jul. 7, 1989 by Tsai et al. which discloses other suitable cationic substituents.

The preparation of cationic sulfonium derivatives is described in U.S. Pat. No. 2,989,520 issued Jun. 1961 to M. Rutenberg et. al, and essentially involves the reaction of a polysaccharide in an aqueous alkaline medium with a beta-halogenoalkylsulfonium salt, vinylsulfonium salt or epoxyalkyl-sulfonium salt. The preparation of cationic phosphonium derivatives is disclosed in U.S. Pat. No. 3,077,469 issued Feb. 12, 1963 to A. Aszalos and involves reaction of a polysaccharide in an aqueous alkaline medium with a betahalogenoalkylphosphonium salt.

Other suitable cationic polysaccharides may be provided using reagents and methods that are well known in the art as illustrated in the above noted references. Normally, the cation group is added to the polysaccharide before forming the aldehyde because of the ease in handling and preparation. If the aldehyde is formed first in the dry form, it is difficult to redisperse. The amount of cationic substituents on the polysaccharide can be varied and generally a degree of substitution (D.S.) of from about 0.005 to 1.5 and preferably from about 0.01 to 0.5 will be used. While larger amounts of cationic substituents or higher degrees of substituents (D.S.) could be used, they are more costly and difficult to make and therefore not economically attractive. The term "degree of substitution" (D.S.) as used herein is meant the average number of sites or substituent groups per anhydrohexose or anhydropentose units.

The polysaccharides useful as base materials, as described above, are galactose containing polysaccharides that have the galactose configuration in the $C_4$ position. When oxidized in accordance with this invention, using the enzyme. galactose oxidase, an aldehyde is formed at a specific position of the polysaccharide, i.e., the $C_6$-OH of the galactose unit. The oxidation reaction is carried out by dispersing the selected polysaccharide in aqueous solution and then adding the enzyme galactose oxidase under an oxygen atmosphere. The reaction is allowed to proceed for a sufficient period of time to allow complete oxidation or until the desired degree of oxidation, i.e., aldehyde content, has been attained. In carrying out the oxidation reaction of the galactose containing polysaccharide with the enzyme galactose oxidase, the rate and completeness of the reaction, like most enzyme catalytic reactions, are dependent on the concentration of the catalyst (as defined by the amount of active units) and substrate, as well as the temperature and pH. The aldehyde content is expressed in terms of dextrose equivalent (D.E.) which is the reducing value of the formed aldehyde derivative and is determined using the method described in Example II. The formed aldehyde derivative will preferably have a reducing value or aldehyde content of at least 5 D.E. and more preferably at least 10 D.E. The maximum D.E. value or aldehyde content will depend on the particular polysaccharide base material that is used. For example, in the case of guar gum which typically has a galactose/mannose ratio of about 38/62, the D.E. may approach 40 and in the case of other polysaccharides may be even higher (see "Carbohydrate Research" by B. V. McCleary, 71, (1979) p, 216, for different polysaccharide galactose/mannose ratios).

The aldehyde cationic polysaccharide derivatives of this invention are useful as paper additives particularly to improve dry and wet strength and especially temporary wet strength properties. These aldehyde cationic derivatives may be used as beater additives, although their addition to the pulp may occur at any point in the paper-making process prior to the ultimate conversion of the wet pulp into a dry web or sheet. Thus, for example they may be added to the pulp while the latter is in the hydropulper, beater, various stock chests or headbox. The derivative may also be sprayed onto the wet web.

The aldehyde cation derivatives may effectively be used for addition to pulp prepared from any type of cellulosic fibers, synthetic fibers, or combination thereof. Among the cellulose materials which may be used are bleached and unbleached sulfite, bleached and unbleached soda, neutral sulfite, semi-chemical chemiground wood, ground wood or any combination of these fibers. Fibers of the viscous rayon or regenerated cellulose type may also be used, if desired.

Any desired inert mineral fillers may be added to the pulp which is to be modified with the aldehyde cation derivatives herein. Such materials include clay, titanium dioxide, talc, calcium carbonate, calcium sulfate and diatomaceous earths. Rosin or synthetic internal size may also be present, if desired.

The proportion of the aldehyde cation derivative to be incorporated into the paper pulp may vary in accordance with the particular pulp involved and the properties desired (e.g., wet strength temporary wet strength or dry strength). In general, it is preferred to use about 0.05 to 15% and more preferably about 0.1 to 5% of the derivative based on the dry weight of the pulp, within the preferred range the precise amount which is used will depend upon the type of pulp being used, the specific operating conditions, the particular end use for which the paper is intended, and the particular property to be imparted. The use of amounts greater than 5% is not precluded, but is ordinarily unnecessary in order to achieve the desired results.

The following examples will more fully illustrate the embodiments of this invention. In the examples, all parts and percentages are by weight and all temperatures in degrees Celsius unless otherwise noted.

EXAMPLE I

This example describes the preparation of cationic derivatives of galactose containing polysaccharides, i.e., guar gum, tamarind gum and locust bean gum.

One hundred (100) g (dry basis) of guar gum was slurried into 285 ml. of isopropanol and 3 g of sodium hydroxide along with 1 g of borax dissolved in 80 ml $M_2O$ was added to the slurry. While under good agitation, 5 g of 3-chloro-1-hydroxypropyl-trimethylammonium chloride (Dow Quat 188) was added to the slurry and the mixture was allowed to react at 40° C. for 16 hours under nitrogen atmosphere. The mixture was then neutralized with hydrochloric acid (18% in isopropanol) to a pH of B, filtered and washed three times with 80% aqueous isopropanol. The sample was then air dried and used for the galactose oxidase treatment procedure in Example II. Additional samples of de-oiled tamarind gum and locust bean gum were prepared using the same procedure described above.

Galactose oxidase treated cationic gums were prepared in the following manner.

Ten (10) g of cationic guar gum prepared in Example I was added slowly along with 1 g of preservative Dowcide A to 1 liter of deionized water under good agitation. The pH of the dispersion was adjusted to 3 by adding phosphoric acid, held for about 30 minutes and then readjusted to 7. The mixture was then heated in a boiling water bath for one hour, cooled to room temperature followed by the addition of galactose oxidase (3500units) obtained from Sigma Chemical Co. (one unit has activity of a $\Delta A_{425}$ of 1.0 per minute at pH 6.0 in 25° C., in a peroxidase and o-tolidine system) and catalase (250,000 units) obtained from Sigma Chemical Co. (one unit will decompose 1.0 μmole of $H_2O_2$ per minute at pH 7.0 at 25° C. while the $H_2O_2$ concentration falls from 10.3 to 9.2 mM) to remove $H_2O_2$ which is generated during the reaction. The reaction was allowed to proceed under oxygen atmosphere until a desirable aldehyde content (degree of oxidation) was achieved. The aldehyde content was determined and expressed as dextrose equivalent (D.E.) by the method described below. The reaction was stopped by deactivating the Enzyme in a boiling water bath for 30 minutes.

Samples of the cationic tamarind gum and locust bean gum prepared in Example I were also tested with galactose oxidase in the same manner.

The following procedure adopted from M, Macleod and R. Robson [Biochem J. 23, 517(1929)] with modification was used to estimate the reducing value (aldehyde content) of the galactose oxidase treated cationic gums.

A standard curve for dextrose was prepared by titrating 1, 5, and 10 mg samples of dextrose.

A known amount of dextrose was added to a 50 cc solution of $1.58 \times 10^{-3}$ M $I_2$, $1.87 \times 10^{-3}$ M KI and $3.74 \times 10^{-3}$ M KCl followed by 10 cc of $6.1 \times 10^{-4}$ M sodium solution. The mixture was brought to a total volume of 110 cc under good stirring for one hour. Ten (10) cc of 1 N $H_2SO_4$ was added and the solution titrated with 0.005 N sodium carbonate stabilized sodium thiosulfate solution using three drops of 1% solubilized starch solution as indicator.

For experimental samples, 20 $m_9$ of the galactose oxidase treated gums was used and the reducing value of the formed aldehyde was determined as dextrose equivalent (D.E.) by calculating the equivalent of iodine consumed with reference to the standard dextrose curve. The results shown as aldehyde Content (D.E.) are shown in the table found in the next example (Example III).

EXAMPLE III

This example describes and compares the use of the aldehyde, cationic derivatives of galactose containing polysaccharides of this invention as paper strength additives.

Paper hand sheets containing the test and control additives were prepared in the following manner. To a headbox containing 12 liters of water (pH 7), 1.2 g of northern softwood kraft fiber (640 CSF—Canadian Standard Freeness) dispersed in 400 cc of water was added. Under good agitation, the additive was added at 10 lb/ton of fibers at 0.5% concentration (w/w). The mixture was drained through a 94 mesh paper machine wire, the wet sheet then put between blotters and predried in a Noble & Wood drum dryer. The blotters were removed and the sheet cured in an oven at 105° C. for 30 minutes. Before testing for strength performance, the sheet was preconditioned in a constant temperature room with 50% relative humidity for at least two hours.

In the paper tests, the tensile strengths are reported as breaking length (m.). The breaking length is the calculated limiting length of a strip of uniform width, beyond which, if such a strip were suspended by one end, it would break of its own weight. The breaking length (air dry) in meters (m.) is calculated using the formula B.L.=102,000 T/R=3,658 T'/R', where T is tensile strength in kN./m., T' is tensile strength in lb./in., R is grammage (air dry) in g./m.$^2$, and R' is weight per unit area (air dry in lb./1000 ft.$^2$). Paper specimens are selected in accordance with TAPPI T 400 sampling procedure. Those evaluated for wet strength and temporary wet strength were saturated with distilled water by immersion and/or soaking until the paper sample was thoroughly wetted. The strength was evaluated in accordance with TAPPI T 494 om-82. The measurements were carried out using a constant rate of elongation apparatus, i-e., a Finch wet strength device which is described in TAPPI Procedure T 456 om-82 (1982). The dry strength was evaluated in accordance with TAPPI T 494 om-81.

The table below illustrates the paper strength improvement obtained by using the galactose oxidase treated cationic guar gum.

| | Aldehyde* Content (D.E.) | Paper Strength** Dry Tensile (B.L.-m) | Wet Tensile (5 sec) (B.L.-m) |
|---|---|---|---|
| 1) Unmodified guar gum | 0 | 1825 | 45 |
| 2) Guar gum treated with Dow Quat. 188 | | | |
| 2.5% | 0 | 1709 | 45 |
| 5.0% | 0 | 1738 | 47 |
| 3) Unmodified guar gum treated with galactose oxidase | 13.5 | 1856 | 246 |
| 4) Guar gum treated with 5% Dow Quat. and galactose oxidase | 10.5 | 2377 | 397 |

*Aldehyde content expressed as dextrose equivalent (D.E.) and determined by iodometric method using glucose as reference standard = 100
**Addition level of gum: 10 lbs/ton of pulp The results show that paper strength was not improved using cation modification alone and only the wet strength was improved with galactose oxidase treatment. However, using both cationic modification and galactose oxidase treatment both the wet and dry strengths were significantly improved.

EXAMPLE IV

This example illustrates the use of galactose oxidase treated cationic de-oiled tamarind gum as a paper strength additive following the same procedure described in Example III.

| | Aldehyde* Content (D.E.) | Paper Strength Dry Tensile (B.L.-m) | Wet Tensile (5 sec) (B.L.-m) |
|---|---|---|---|
| 1) De-oiled tamarind gum | 0 | 1586 | 38 |
| 2) De-oiled tamarind gum treated with 5% Dow Quat. | 0 | 1676 | 37 |
| 3) De-oiled tamarind gum treated with galactose oxidase | 10.8 | 1563 | 116 |
| 4) De-oiled tamarind gum treated with 5% Dow Quat. and galactose oxidase | 9.4 | 1720 | 218 |
| 5) Purified tamarind gum (Glyloid 3S) treated with 5% Dow Quat. and galactose oxidase | 15.7 | 2044 | 265 |

The results show the significant improvement in both wet and dry strength that is obtained when using the tamarind gum having both cationic modification and galactose oxidase treatment.

EXAMPLE V

This example illustrates the effectiveness of galactose oxidase treated cationic locust bean gum as a paper strength additive. The same procedure described in Example III was followed.

| | Aldehyde* Content (D.E.) | Paper Strength Dry Tensile (B.L.-m) | Wet Tensile (5 sec) (B.L.-m) |
|---|---|---|---|
| 1) Unmodified locust bean gum | — | 1688 | 43 |
| 2) Locust bean gum treated with 5% Dow Quat. | — | 1704 | 41 |
| 3) Locust bean gum treated with 5% Dow Quat. and galactose oxidase | 8.8 | 1816 | 224 |
| | 11.9 | 2041 | 274 |
| | 13.9 | 1925 | 305 |

The results show the significant improvement in both wet and dry strength that is obtained when using the locust bean gum having both cationic modification and galactose oxidase treatment.

What is claimed:

1. In the method of making paper having dry strength, wet strength, temporary wet strength or combinations thereof, the step which consists essentially of adding, as a strength aid, to the pulp containing stock at any stage prior to forming a web, an effective amount of an aldehyde cationic polysaccharide derivative, that is obtained from a naturally occurring galactose containing polysaccharide which is cationized and subsequently oxidized by reacting with galactose oxidase to provide an aldehyde group in the $C_6$ position of the galactose unit and wherein the aldehyde cationic polysaccharide derivative has a cationic content represented by a D.S. of from about 0.005 to 1.5 and an aldehyde content represented by a D.E. of from about 5 to 40.

2. The method of claim 1 wherein the polysaccharide is a polygalactomannan gum.

3. The method of claim 1 wherein the polysaccharide is selected from the group consisting of guar gum, locust bean gum, tamarind gum and gum arabic.

4. The method of claim 1 wherein the aldehyde cation polysaccharide derivative contains tertiary alkyl or aryl amine or quaternary alkyl or aryl ammonium ether cationic groups.

5. The method of claim 1 wherein the polysaccharide derivative is added in an amount of from about 0.05 to 15% by weight based on the dry weight of pulp.

6. The method of claim 5 wherein the polysaccharide is selected from the group consisting of guar gum, locust bean gum, taramind gum and gum arabic.

7. The method of claim 6 wherein the aldehyde cationic polysaccharide derivative contains tertiary alkyl or aryl amine or quaternary alkyl or aryl ammonium ether cationic groups.

8. The method of claim 7 wherein the aldehyde cation polysaccharide derivative has a cationic content represented by a D.S. of from about 0.01 to 0.5 and an aldehyde content represented by a D.E. of from about 10 to 40.

* * * * *